(12) United States Patent
Lipkens et al.

(10) Patent No.: US 9,675,906 B2
(45) Date of Patent: Jun. 13, 2017

(54) ACOUSTOPHORETIC CLARIFICATION OF PARTICLE-LADEN NON-FLOWING FLUIDS

(71) Applicant: FloDesign Sonics, Inc., Wilbraham, MA (US)

(72) Inventors: Bart Lipkens, Hampden, MA (US); Jeff King, Coventry, CT (US); David Sokolowski, Wilbraham, MA (US); Anthony B. Masi, Wilbraham, MA (US); Brian T. Kennedy, Wilbraham, MA (US); Brian McCarthy, Ludlow, MA (US); Benjamin Ross-Johnsrud, Wilbraham, MA (US); Jason Dionne, Simsbury, CT (US); Dane Mealey, Springfield, MA (US); Jason Barnes, Westfield, MA (US)

(73) Assignee: FLODESIGN SONICS, INC., Wilbraham, MA (US)

( * ) Notice: Subject to any disclaimer, the term of this patent is extended or adjusted under 35 U.S.C. 154(b) by 0 days.

(21) Appl. No.: 14/870,952

(22) Filed: Sep. 30, 2015

(65) Prior Publication Data

US 2016/0089620 A1 Mar. 31, 2016

Related U.S. Application Data

(60) Provisional application No. 62/057,514, filed on Sep. 30, 2014.

(51) Int. Cl.
*B01D 21/28* (2006.01)
*C12N 13/00* (2006.01)
(Continued)

(52) U.S. Cl.
CPC .......... *B01D 21/283* (2013.01); *B06B 1/0622* (2013.01); *B06B 1/0644* (2013.01);
(Continued)

(58) Field of Classification Search
CPC .......... B01D 21/283; B01D 2021/0081; B01D 43/00; B01D 21/28; B01J 19/10; C02F 1/36
See application file for complete search history.

(56) References Cited

U.S. PATENT DOCUMENTS

| | | | |
|---|---|---|---|
| 2,667,944 A | 2/1954 | Crites | |
| 3,555,311 A | 1/1971 | Weber | |
| 4,055,491 A | 10/1977 | Porath-Furedi | |
| 4,158,629 A | 6/1979 | Sawyer | |
| 4,165,273 A | 8/1979 | Azarov et al. | |
| 4,173,725 A | 11/1979 | Asai et al. | |
| 4,204,096 A | 5/1980 | Barcus et al. | |
| 4,398,325 A | 8/1983 | Piaget et al. | |
| 4,666,595 A | 5/1987 | Graham | |
| 4,699,588 A | 10/1987 | Zinn et al. | |
| 4,743,361 A | 5/1988 | Schram | |
| 4,759,775 A | 7/1988 | Peterson et al. | |
| 4,983,189 A | 1/1991 | Peterson et al. | |

(Continued)

FOREIGN PATENT DOCUMENTS

DE 30 27 433 A1 2/1982
EP 0 292 470 B1 11/1988
(Continued)

OTHER PUBLICATIONS

International Search Report and Written Opinion dated Dec. 28, 2015 for PCT Application Serial No. PCT/US2015/053200.
(Continued)

*Primary Examiner* — Walter D Griffin
*Assistant Examiner* — Cameron Allen
(74) *Attorney, Agent, or Firm* — Richard M. Klein; Fay Sharpe LLP

(57) ABSTRACT

Acoustophoretic devices for separating particles from a non-flowing host fluid are disclosed. The devices include a substantially acoustically transparent container and a separation unit, with the container being placed within the separation unit. An ultrasonic transducer in the separation unit creates a planar or multi-dimensional acoustic standing wave within the container, trapping particles disposed within the non-flowing fluid and causing them to coalesce or agglomerate, then separate due to buoyancy or gravity forces.

20 Claims, 10 Drawing Sheets

(51) Int. Cl.
   *C12M 1/00* (2006.01)
   *B06B 1/06* (2006.01)
(52) U.S. Cl.
   CPC .............. *C12M 47/04* (2013.01); *C12N 13/00* (2013.01); *B06B 2201/71* (2013.01)

(56) References Cited

U.S. PATENT DOCUMENTS

| | | |
|---|---|---|
| 5,085,783 A | 2/1992 | Feke et al. |
| 5,225,089 A | 7/1993 | Benes et al. |
| 5,371,429 A | 12/1994 | Manna |
| 5,395,592 A | 3/1995 | Bolleman et al. |
| 5,431,817 A | 7/1995 | Braatz et al. |
| 5,443,985 A | 8/1995 | Lu et al. |
| 5,452,267 A | 9/1995 | Spevak |
| 5,484,537 A | 1/1996 | Whitworth |
| 5,527,460 A | 6/1996 | Trampler et al. |
| 5,560,362 A | 10/1996 | Sliwa, Jr. et al. |
| 5,594,165 A | 1/1997 | Madanshetty |
| 5,604,301 A | 2/1997 | Mountford et al. |
| 5,626,767 A | 5/1997 | Trampler et al. |
| 5,688,405 A | 11/1997 | Dickinson et al. |
| 5,711,888 A | 1/1998 | Trampler et al. |
| 5,831,166 A | 11/1998 | Kozuka et al. |
| 5,902,489 A | 5/1999 | Yasuda et al. |
| 5,912,182 A | 6/1999 | Coakley et al. |
| 5,951,456 A | 9/1999 | Scott |
| 6,090,295 A | 7/2000 | Raghavarao et al. |
| 6,166,231 A | 12/2000 | Hoeksema |
| 6,205,848 B1 | 3/2001 | Faber et al. |
| 6,216,538 B1 | 4/2001 | Yasuda et al. |
| 6,332,541 B1 | 12/2001 | Coakley et al. |
| 6,391,653 B1 | 5/2002 | Letcher et al. |
| 6,487,095 B1 | 11/2002 | Malik et al. |
| 6,592,821 B1 | 7/2003 | Wada et al. |
| 6,649,069 B2 | 11/2003 | DeAngelis |
| 6,763,722 B2 | 7/2004 | Fjield et al. |
| 6,881,314 B1 | 4/2005 | Wang et al. |
| 6,929,750 B2 | 8/2005 | Laurell et al. |
| 6,936,151 B1 | 8/2005 | Lock et al. |
| 7,010,979 B2 | 3/2006 | Scott |
| 7,061,163 B2 | 6/2006 | Nagahara et al. |
| 7,081,192 B1 | 7/2006 | Wang et al. |
| 7,093,482 B2 | 8/2006 | Berndt |
| 7,108,137 B2 | 9/2006 | Lal et al. |
| 7,150,779 B2 | 12/2006 | Meegan, Jr. |
| 7,186,502 B2 | 3/2007 | Vesey |
| 7,191,787 B1 | 3/2007 | Redeker et al. |
| 7,322,431 B2 * | 1/2008 | Ratcliff .................. B01D 17/00 166/177.1 |
| 7,331,233 B2 | 2/2008 | Scott |
| 7,340,957 B2 | 3/2008 | Kaduchak et al. |
| 7,373,805 B2 | 5/2008 | Hawkes et al. |
| 7,541,166 B2 | 6/2009 | Belgrader et al. |
| 7,601,267 B2 | 10/2009 | Haake et al. |
| 7,673,516 B2 | 3/2010 | Janssen et al. |
| 7,837,040 B2 | 11/2010 | Ward et al. |
| 7,846,382 B2 | 12/2010 | Strand et al. |
| 7,968,049 B2 | 6/2011 | Takahashi et al. |
| 8,080,202 B2 | 12/2011 | Takahashi et al. |
| 8,256,076 B1 | 9/2012 | Feller |
| 8,266,950 B2 | 9/2012 | Kaduchak et al. |
| 8,273,253 B2 | 9/2012 | Curran |
| 8,273,302 B2 | 9/2012 | Takahashi et al. |
| 8,309,408 B2 | 11/2012 | Ward et al. |
| 8,319,398 B2 | 11/2012 | Vivek et al. |
| 8,334,133 B2 | 12/2012 | Fedorov et al. |
| 8,387,803 B2 | 3/2013 | Thorslund et al. |
| 8,679,338 B2 | 3/2014 | Rietman et al. |
| 2002/0134734 A1 | 9/2002 | Campbell et al. |
| 2003/0195496 A1 | 10/2003 | Maguire |
| 2003/0209500 A1 | 11/2003 | Kock et al. |
| 2003/0230535 A1 | 12/2003 | Affeld et al. |
| 2004/0016699 A1 | 1/2004 | Bayevsky |
| 2005/0196725 A1 | 9/2005 | Fu |
| 2006/0037915 A1 | 2/2006 | Strand et al. |
| 2007/0027618 A1 | 2/2007 | Sands et al. |
| 2007/0053795 A1 | 3/2007 | Laugharn, Jr. et al. |
| 2007/0224676 A1 | 9/2007 | Haq |
| 2007/0267351 A1 | 11/2007 | Roach et al. |
| 2007/0284299 A1 | 12/2007 | Xu et al. |
| 2008/0217259 A1 | 9/2008 | Siversson |
| 2008/0264716 A1 | 10/2008 | Kuiper et al. |
| 2009/0029870 A1 | 1/2009 | Ward et al. |
| 2009/0045107 A1 | 2/2009 | Ward et al. |
| 2009/0053686 A1 | 2/2009 | Ward et al. |
| 2009/0098027 A1 | 4/2009 | Tabata et al. |
| 2009/0178716 A1 | 7/2009 | Kaduchak et al. |
| 2009/0194420 A1 | 8/2009 | Mariella, Jr. et al. |
| 2009/0226994 A1 | 9/2009 | Lemor et al. |
| 2009/0295505 A1 | 12/2009 | Mohammadi et al. |
| 2010/0000945 A1 | 1/2010 | Gavalas |
| 2010/0078384 A1 | 4/2010 | Yang |
| 2010/0124142 A1 | 5/2010 | Laugharn et al. |
| 2010/0192693 A1 | 8/2010 | Mudge et al. |
| 2010/0193407 A1 | 8/2010 | Steinberg et al. |
| 2010/0206818 A1 | 8/2010 | Leong et al. |
| 2010/0255573 A1 | 10/2010 | Bond et al. |
| 2010/0261918 A1 | 10/2010 | Chianelli et al. |
| 2010/0317088 A1 | 12/2010 | Radaelli et al. |
| 2010/0323342 A1 | 12/2010 | Gonzalez Gomez et al. |
| 2010/0330633 A1 | 12/2010 | Walther et al. |
| 2011/0003350 A1 | 1/2011 | Schafran et al. |
| 2011/0024335 A1 | 2/2011 | Ward et al. |
| 2011/0092726 A1 | 4/2011 | Clarke |
| 2011/0095225 A1 | 4/2011 | Eckelberry et al. |
| 2011/0123392 A1 | 5/2011 | Dionne et al. |
| 2011/0154890 A1 | 6/2011 | Holm et al. |
| 2011/0166551 A1 | 7/2011 | Schafer |
| 2011/0262990 A1 | 10/2011 | Wang et al. |
| 2011/0281319 A1 | 11/2011 | Swayze et al. |
| 2011/0309020 A1 | 12/2011 | Rietman et al. |
| 2012/0088295 A1 | 4/2012 | Yasuda et al. |
| 2012/0175012 A1 | 7/2012 | Goodwin et al. |
| 2012/0328477 A1 | 12/2012 | Dionne et al. |
| 2012/0329122 A1 | 12/2012 | Lipkens et al. |
| 2013/0277316 A1 | 10/2013 | Dutra et al. |
| 2013/0284271 A1 | 10/2013 | Lipkens et al. |
| 2014/0011240 A1 | 1/2014 | Lipkens et al. |
| 2014/0017758 A1 | 1/2014 | Kniep et al. |
| 2014/0102947 A1 | 4/2014 | Baym et al. |
| 2014/0141413 A1 | 5/2014 | Laugham, Jr. et al. |

FOREIGN PATENT DOCUMENTS

| | | |
|---|---|---|
| EP | 1 254 669 B1 | 11/2002 |
| GB | 2 420 510 A | 5/2006 |
| WO | WO 87/07178 A1 | 12/1987 |
| WO | WO 98/17373 | 4/1998 |
| WO | WO 00/41794 | 7/2000 |
| WO | WO 02/072234 A1 | 9/2002 |
| WO | WO 2009/111276 A1 | 9/2009 |
| WO | WO 2009/144709 A1 | 12/2009 |
| WO | WO 2010/024753 A1 | 4/2010 |
| WO | WO 2011/023949 A2 | 3/2011 |
| WO | WO 2011/025890 A1 | 3/2011 |
| WO | WO 2011/027146 A2 | 3/2011 |
| WO | WO 2011/161463 A2 | 12/2011 |
| WO | WO 2013/043297 A1 | 3/2013 |
| WO | WO 2013/055517 A1 | 4/2013 |

OTHER PUBLICATIONS

Alvarez et al.; Shock Waves, vol. 17, No. 6, pp. 441-447, 2008.
Benes et al.; Ultrasonic Separation of Suspended Particles, 2001 IEEE Ultrasonics Symposium; Oct. 7-10, 2001; pp. 649-659; Atlanta, Georgia.
Castro; Tunable gap and quantum quench dynamics in bilayer graphene; Jul. 13, 2010; Mathematica Summer School.
Cravotto et al.; Ultrasonics Sonochemistry, vol. 15, No. 5, pp. 898-902, 2008.

(56) References Cited

OTHER PUBLICATIONS

Garcia-Lopez, et al; Enhanced Acoustic Separation of Oil-Water Emulsion in Resonant Cavities. The Open Acoustics Journal. 2008, vol. 1, pp. 66-71.
Hill et al.; Ultrasonic Particle Manipulation; Microfluidic Technologies for Miniaturized Analysis Systems, Jan. 2007, pp. 359-378.
Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.
Latt et al.; Ultrasound-membrane hybrid processes for enhancement of filtration properties; Ultrasonics sonochemistry 13.4 (2006): 321-328.
Lipkens et al.; Frequency sweeping and fluid flow effects on particle trajectories in ultrasonic standing waves; Acoustics 08, Paris, Jun. 29-Jul. 4, 2008.
Lipkens et al.; Prediction and measurement of particle velocities in ultrasonic standing waves; J. Acoust. Soc. Am., 124 No. 4, pp. 2492 (A) 2008.
Lipkens et al.; Separation of micron-sized particles in macro-scale cavities by ultrasonic standing waves; Presented at the International Congress on Ultrasonics, Santiago; Jan. 11-17, 2009.
Lipkens et al.; The effect of frequency sweeping and fluid flow on particle trajectories in ultrasonic standing waves; IEEE Sensors Journal, vol. 8, No. 6, pp. 667-677, 2008.
Lipkens et al., Macro-scale acoustophoretic separation of lipid particles from red blood cells, The Journal of the Acoustical Society of America, vol. 133, Jun. 2, 2013, p. 045017, XP055162509, New York, NY.
Meribout et a.; An Industrial-Prototype Acoustic Array for Real-Time Emulsion Layer Detection in Oil Storage Tanks; IEEE Sensors Journal, vol. 9, No. 12, Dec. 2009.
Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.
Pangu et al.; Droplet transport and coalescence kinetics in emulsions subjected to acoustic fields; Ultrasonics 46, pp. 289-302 (2007).
Ponomarenko et al.; Density of states and zero Landau level probed through capacitance of graphene; Nature Nanotechnology Letters, Jul. 5, 2009; DOI: 10.1038/NNANO.2009.177.
Seymour et al, J. Chem. Edu., 1990, 67(9), p. 763, published Sep. 1990.
Annex to Form PCT/ISA/206—Communication Relating to the Results of the Partial International Search Report, dated Jul. 18, 2013.
European Search Report of European Application No. 11769474.5 Dated Oct. 10, 2012.
International Search Report and Written Opinion dated Dec. 20, 2011, for corresponding PCT application No. PCT/US2011/032181.
International Search Report and Written Opinion dated Feb. 27, 2012, for PCT application No. PCT/US2011/040787.
International Search Report and Written Opinion of International Application No. PCT/US2013/037404 Dated Jun. 21, 2013.
International Search Report and Written Opinion of International Application No. PCT/US2013/050729 Dated Sep. 25, 2013.
International Search Report for corresponding PCT Application Serial No. PCT/US2014/015382 dated May 6, 2014.
Phys. Org. "Engineers develop revolutionary nanotech water desalination membrane." Nov. 6, 2006. http://phys.org/news82047372.html.
"Proceedings of the Acoustics 2012 Nantes Conference," Apr. 23-27, 2012, Nantes, France, pp. 278-282.
Sony New Release: <http://www.sony.net/SonyInfo/News/Press/201010/10-137E/index.html>.

* cited by examiner

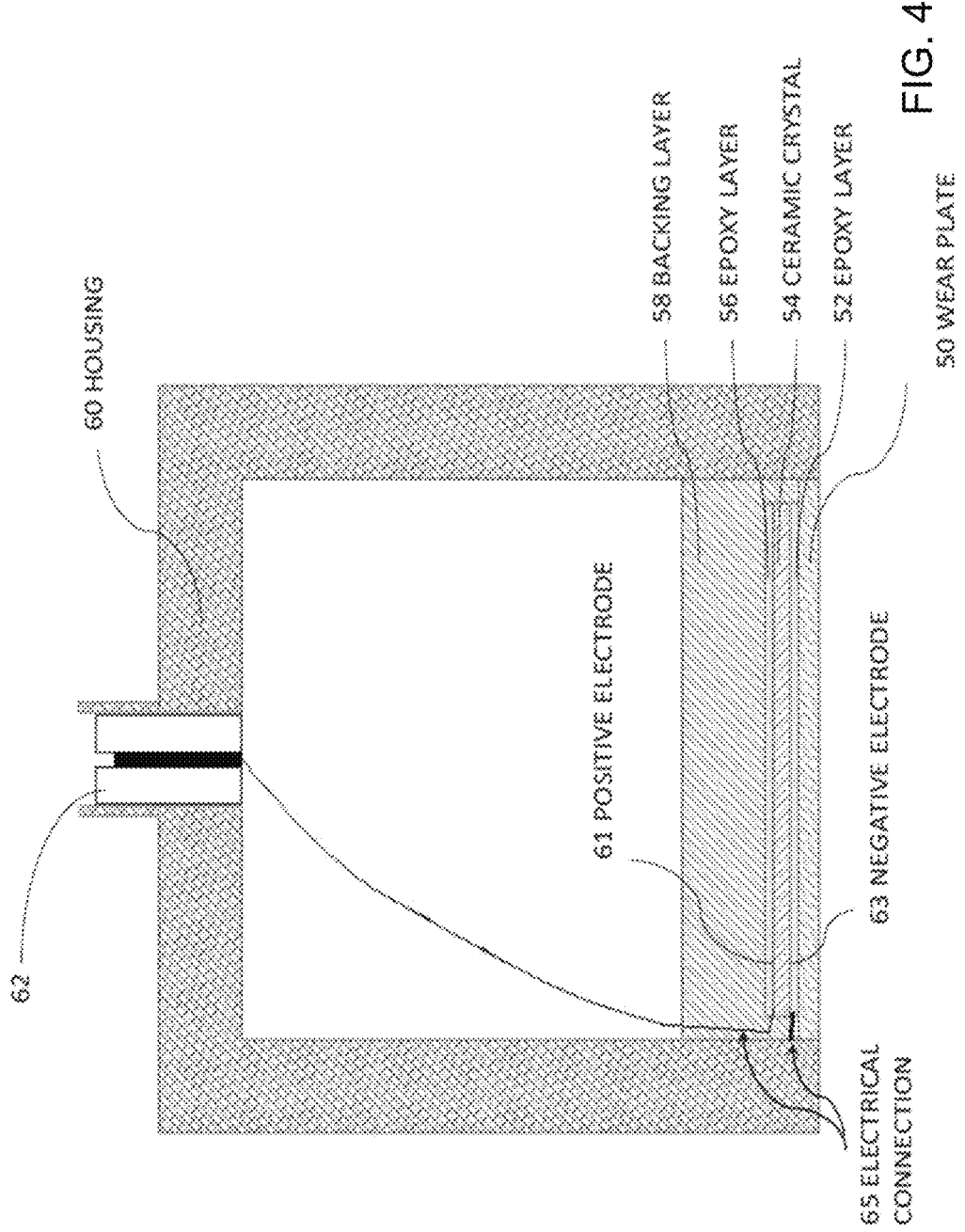

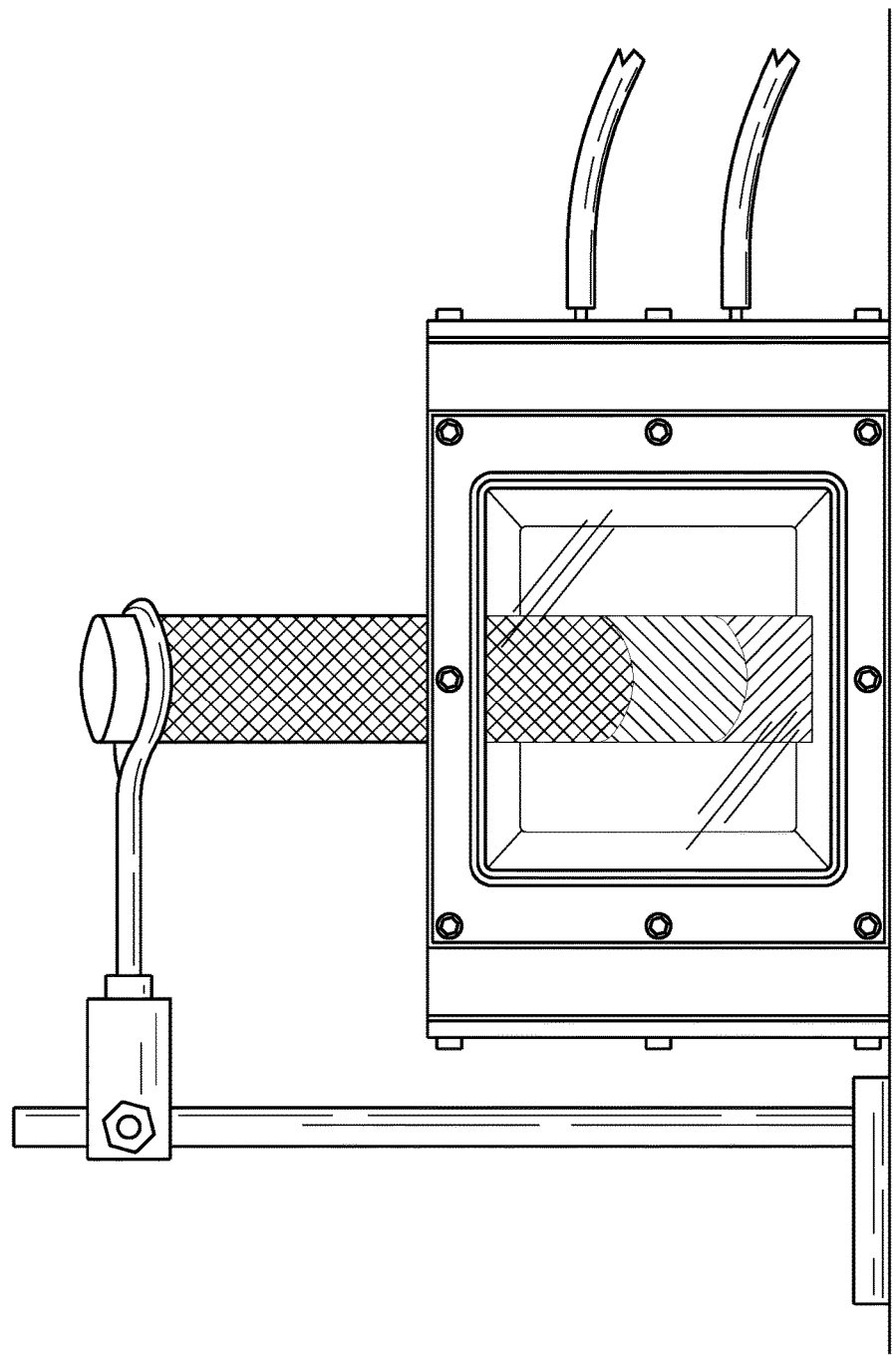

ACOUSTOPHORETIC CLARIFICATION OF PARTICLE-LADEN NON-FLOWING FLUIDS

CROSS-REFERENCE TO RELATED APPLICATIONS

This application claims priority to U.S. Provisional Patent Application Ser. No. 62/057,514, filed on Sep. 30, 2014, which is incorporated herein by reference in its entirety.

BACKGROUND

Acoustophoresis is the separation of particles and secondary fluids from a primary or host fluid using high intensity acoustic standing waves, and without the use of membranes or physical size exclusion filters. It has been known that high intensity standing waves of sound can exert forces on particles in a fluid when there is a differential in both density and/or compressibility, otherwise known as the acoustic contrast factor. The pressure profile in a standing wave contains areas of local minimum pressure amplitudes at its nodes and local maxima at its anti-nodes. Depending on the density and compressibility of the particles, they will be trapped at the nodes or anti-nodes of the standing wave. The higher the frequency of the standing wave, the smaller the particles that can be trapped due to the pressure of the standing wave. The acoustophoretic process is typically performed on a moving fluid stream.

There are many applications where there is a need to clarify a fluid that contains particles or droplets, or separate the secondary phase from the host fluid. In certain situations it can be advantageous to execute such a process in a batch or semi-batch mode, especially when the concentration of the secondary phase is large, e.g., exceeding 1% by volume concentration, or e.g., exceeding 10%. Applications are in settling tanks, yeast separation processes in food and beverage industries, mammalian cell clarification in biopharmacy, and red and white blood cells from plasma.

BRIEF DESCRIPTION

The present disclosure relates, in various embodiments, to the use of ultrasonic energy in a standing wave to separate particles or secondary fluids in batch mode from a discrete volume of a fluid containing a mixture of a host fluid and particles/secondary fluid. The discrete volume of fluid is non-flowing, i.e. the fluid is not being pumped, flowed, or displaced by a second volume of fluid. Clarification of the discrete volume of fluid is accomplished using an acoustophoretic device. As a result, the discrete volume of fluid is separated into two portions, a portion with an increased concentration of particles and a portion with a decreased concentration of particles. The acoustophoresis separation process traps particles and droplets in their stable trapping locations within the acoustic field. A strong three-dimensional acoustic field further creates tightly packed clusters at these locations such that the gravity/buoyancy force becomes dominant, resulting in continuous settling of clusters or clumps of particles when they are heavier than the host liquid or rise out of suspension when the particles or droplets are lighter than the host fluid.

In various embodiments, the acoustophoretic device comprises a substantially acoustically transparent container having an upper end and a lower end; and a separation unit defined by one or more walls. The separation unit includes at least one ultrasonic transducer having a piezoelectric material driven by a voltage signal to create an acoustic standing wave in the separation unit through the container, and the separation unit is separable from the container.

Generally, the container holds the volume of fluid therein. The container is generally formed from a substantially acoustically transparent material, such as plastic, glass, polycarbonate, low-density polyethylene, and high-density polyethylene, having an appropriate thickness based on the frequency of the acoustic standing wave. The container may be a plastic bottle or plastic bag.

In certain embodiments, the separation unit includes two ultrasonic transducers. When the use of two ultrasonic transducers is desired, the two ultrasonic transducers may be located on a common wall of the separation unit such that only a single reflector is necessary to propagate the standing wave in the separation unit. Alternatively, the two ultrasonic transducers may be located opposite to each other, thereby creating waves that cross one another.

In some embodiments, a wall of the separation unit includes a viewing window for viewing the separation occurring in the lower end of the container. The viewing window can further serve to allow the desired placement of the container in the separation unit.

Also disclosed herein is a method for clarifying a discrete volume of fluid medium containing particles using the container and separation unit previously described. The method generally comprises the steps of introducing the discrete volume of fluid medium to a container having an upper end and a lower end; placing the container into a separation unit defined by at least one wall, the separation unit including at least one ultrasonic transducer having a piezoelectric material capable of creating an acoustic standing wave in the separation unit by reflecting incident waves off of a reflector located opposite the at least one ultrasonic transducer; and driving the at least one ultrasonic transducer to create the acoustic standing wave in the separation unit to separate the particles from the discrete volume of fluid medium.

Generally, driving the ultrasonic transducer to create the acoustic standing wave results in the creation of nodal lines and lateral forces that trap the particles of the discrete volume of fluid medium in those nodal lines. The particles in those nodal lines cluster, clump, agglomerate, or coalesce and sink to the lower end of the container due to gravitational forces or rise to the upper end of the container due to buoyancy forces. The sinking or rising of the clusters also creates a gravity-driven flow within the discrete volume itself, further enhancing the separation of the phases. In some embodiments, a fluid is interstitial between the container and the separation unit, such that the acoustic standing wave passes through the fluid in the separation unit and the discrete volume of fluid medium in the container.

In certain embodiments, the container may be a disposable separation bag including an exterior surface and an interior volume bounded by the exterior surface. In such embodiments, the ultrasonic transducer is at least partially disposed inward of the exterior surface of the separation bag such that an acoustic standing wave can be created in the interior volume of the bag. This allows for a disposable system whereby solids suspended within the fluid in the bag may be clumped, clustered, or agglomerated, and settle out of solution, and droplets emulsified in the fluid cluster, clump, agglomerate, or coalesce such that buoyancy forces the agglomerated or coalesced droplets to rise out of suspension. The acoustic standing wave field thus creates a clarification of the fluid in the bag. That is, in this arrangement, the cells, cell debris or other solids in the fluid are caught in the acoustic standing wave(s), clumped up into larger groups and fall back into the separation bag due to the force of gravity.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 4 is a cross-sectional diagram of a conventional ultrasonic transducer.

FIG. 10 is a view of an acoustophoretic device of the present disclosure, showing a plastic bag (i.e. the container) partially disposed within a separation unit having an ultrasonic transducer driven by a voltage signal delivered by a BNC cable.

DETAILED DESCRIPTION

Figure 1:
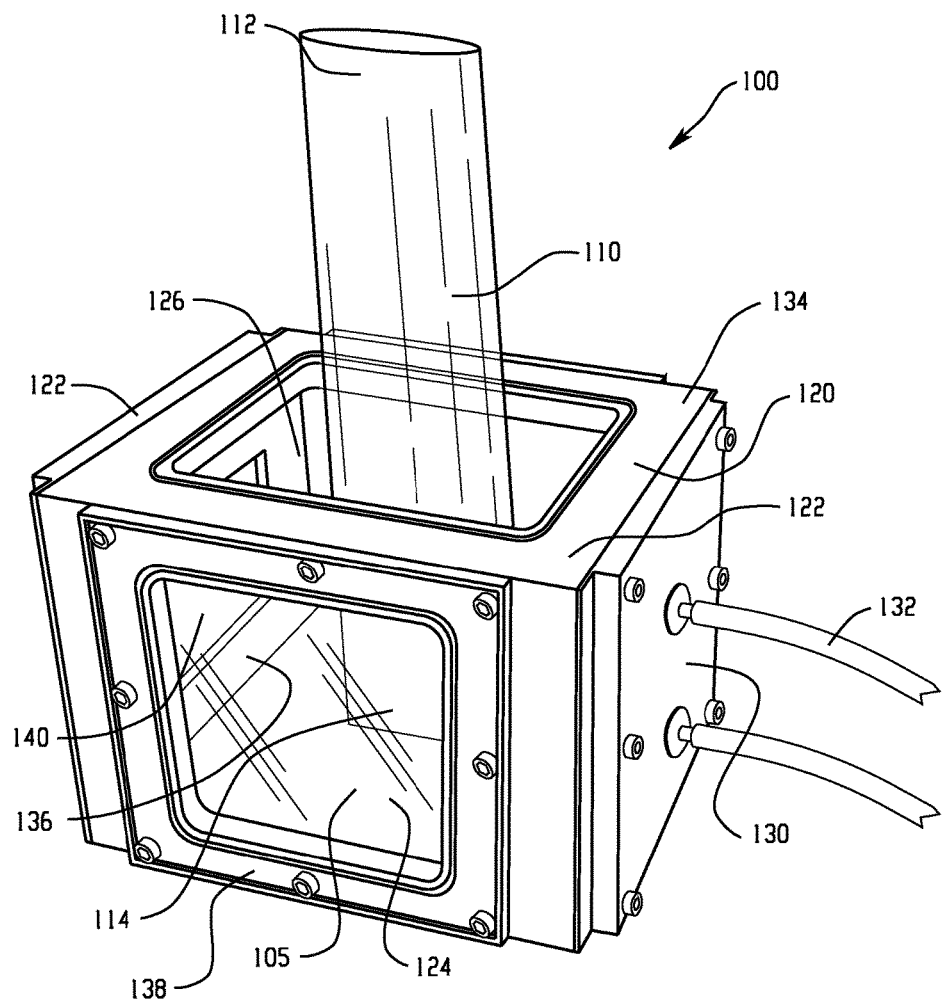
FIG. 1 is a perspective view of one exemplary embodiment of an acoustophoretic device of the present disclosure. A disposable container (e.g. a plastic bag) works in conjunction with a reusable separation unit containing one or more ultrasonic transducers.

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function. Furthermore, it should be understood that the drawings are not to scale.

The singular forms "a," "an," and "the" include plural referents unless the context clearly dictates otherwise.

The term "comprising" is used herein as requiring the presence of the named components/steps and allowing the presence of other components/steps. The term "comprising" should be construed to include the terms "consisting of" and "consisting essentially of", which permit the presence of only the named components/steps and unavoidable impurities, and exclude other components/steps.

All numerical values used herein include values that are the same when reduced to the same number of significant figures and values that differ by less than the experimental error of conventional techniques for measuring that value.

All ranges disclosed herein are inclusive of the recited endpoint and independently combinable (for example, the range of "from 2 grams to 10 grams" is inclusive of the endpoints, 2 grams and 10 grams, and all the intermediate values).

The terms "substantially" and "about" can be used to include any numerical value that can vary without changing the basic function of that value. When used with a range, they also disclose the range defined by the absolute values of the two endpoints, e.g. "about 2 to about 4" also discloses the range "from 2 to 4." The term "about" may refer to plus or minus 10% of the indicated number.

It should be noted that many of the terms used herein are relative terms. For example, the terms "upper" and "lower" are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, i.e. ground level. However, these terms should not be construed to require structures to be absolutely parallel or absolutely perpendicular to each other. For example, a first vertical structure and a second vertical structure are not necessarily parallel to each other. The terms "top" and "bottom" are used to refer to surfaces or ends where the top is always higher than the bottom relative to an absolute reference, i.e. the surface of the earth. The terms "upwards" and "downwards" are also relative to an absolute reference; upwards is always against the gravity of the earth.

The term "parallel" should be construed in its lay sense of two surfaces that maintain a generally constant distance between them, and not in the strict mathematical sense that such surfaces will never intersect when extended to infinity.

The present application refers to "the same order of magnitude." Two numbers are of the same order of magnitude if the quotient of the larger number divided by the smaller number is a value less than 10.

The acoustophoretic separation technology of the present disclosure employs ultrasonic acoustic standing waves to trap particles or a secondary fluid in a volume of fluid containing said particles/secondary fluid. The particles or secondary fluid collect at the nodes or anti-nodes of the acoustic standing wave, depending on the particles' or secondary fluid's acoustic contrast factor relative to the host fluid, forming clusters/clumps/agglomerates/coalesced droplets that continuously fall out of the acoustic standing wave when the clusters have grown to a size large enough to overcome the holding force of the acoustic standing wave (e.g. by coalescence or agglomeration) and the particle/secondary fluid density is higher than the host fluid, or to rise out of the acoustic standing wave when the particle/secondary fluid density is less than the host fluid. The acoustic radiation force is proportional to the particle volume (e.g. the cube of the radius) when the particle is small relative to the wavelength. It is proportional to frequency and the acoustic contrast factor. It also scales with acoustic energy (e.g. the square of the acoustic pressure amplitude). For harmonic excitation, the sinusoidal spatial variation of the force is what drives the particles to the stable axial positions within the standing waves. When the acoustic radiation force exerted on the particles is stronger than the combined effect of fluid drag force and buoyancy and gravitational force, the particle is trapped within the acoustic standing wave field. This results in concentration, agglomeration and/or coalescence of the trapped particles. The strong lateral forces create rapid clustering of particles. Micron-sized particles, e.g., bacteria, mammalian cells, micro-algae, metal particles, yeast, fungi, lipids, oil droplets, red blood cells, white blood cells, platelets, etc, can thus be separated from the host fluid through enhanced gravitational separation. For the case of a suspension with several different particle sizes, it is possible by tuning of the system parameters to settle out the group of particles that are larger in size whereas the group of particles smaller in size can be kept in suspension. These two layers can then be harvested separately. A repeated process can then be used to fractionate groups of different sized particles according to size.

One specific application for the acoustophoresis device is in the processing of bioreactor materials. It is important to be able to separate relatively larger cells and cell debris from the expressed materials that are in the host fluid. The expressed materials are composed of biomolecules such as recombinant proteins or monoclonal antibodies, and are the desired product to be recovered. Through the use of acoustophoresis, the separation of the cells and cell debris is very efficient and leads to very little loss of the expressed materials. This is an improvement over current filtration processes (depth filtration, tangential flow filtration, and the like), which show limited efficiencies at high cell densities, so that the loss of the expressed materials in the filter beds themselves can be up to 5% of the materials produced by the bioreactor. The use of mammalian cell cultures including Chinese hamster ovary (CHO), NS0 hybridoma cells, baby hamster kidney (BHK) cells, insect cells, and human cells (e.g. T-cells, B-cells, stem cells, red blood cells), and living/biological cells in general has proven to be a very efficacious way of producing/expressing the recombinant proteins and monoclonal antibodies required of today's pharmaceuticals. The filtration of the mammalian cells and the mammalian cell debris through acoustophoresis aids in greatly increasing the yield of the bioreactor. As desired, the acoustophoresis process may also be coupled with a standard filtration process upstream or downstream, such as depth filtration, tangential flow filtration (TFF), or other physical filtration processes.

In this regard, the acoustic contrast factor is a function of the ratio of particle to fluid compressibility and particle to fluid density. Most cell types present a higher density and lower compressibility than the medium in which they are suspended, so that the acoustic contrast factor between the cells and the medium has a positive value. As a result, the axial acoustic radiation force (ARF) drives the cells, with a positive contrast factor, to the pressure nodal planes, whereas cells or other particles with a negative contrast factor are driven to the pressure anti-nodal planes. The radial or lateral component of the ARF is larger than the combined effect of fluid drag force and gravitational force. The radial or lateral component drives the cells/particles to specific locations (points) within these planes where they cluster, clump, agglomerate, or coalesce into larger groups, which will then continuously gravity separate from the fluid.

Desirably, the ultrasonic transducer(s) generate a three-dimensional or multi-dimensional acoustic standing wave in the fluid that exerts a lateral force on the suspended particles to accompany the axial force so as to increase the particle trapping and clumping capabilities of the standing wave. Typical results published in literature state that the lateral force is two orders of magnitude smaller than the axial force. In contrast, the technology disclosed in this application provides for a lateral force to be of the same order of magnitude as the axial force (i.e. a multi-dimensional acoustic standing wave). However, in certain embodiments described further herein, combinations of transducers that produce both multi-dimensional acoustic standing waves and planar standing waves are contemplated. For purposes of this disclosure, a standing wave where the lateral force is not the same order of magnitude as the axial force is considered a "planar acoustic standing wave."

For three-dimensional acoustic fields, Gor'kov's formulation can be used to calculate the acoustic radiation force $F_{ac}$ applicable to any sound field. The primary acoustic radiation force $F_{ac}$ is defined as a function of a field potential U, $$F_A = -\nabla(U),$$

where the field potential U is defined as $$U = V_0 \left[ \frac{\langle p^2 \rangle}{2\rho_f c_f^2} f_1 - \frac{3\rho_f \langle u^2 \rangle}{4} f_2 \right],$$

and $f_1$ and $f_2$ are the monopole and dipole contributions defined by $$f_1 = 1 - \frac{1}{\Lambda \sigma^2},$$

$$f_2 = \frac{2(\Lambda - 1)}{2\Lambda + 1},$$

where p is the acoustic pressure, u is the fluid particle velocity, $\Lambda$ is the ratio of cell density $\rho_p$ to fluid density $\rho_f$, a is the ratio of cell sound speed $c_p$ to fluid sound speed $c_f$, $V_o$ is the volume of the cell, and < > indicates time averaging over the period of the wave. Gor'kov's formulation applies to particles smaller than the wavelength. For larger particle sizes, Ilinskii provides equations for calculating the 3D acoustic radiation forces for any particle size. See Ilinskii, *Acoustic Radiation Force on a Sphere in Tissue*, The Journal of the Acoustical Society of America, 132, 3, 1954 (2012), which is incorporated herein by reference.

Perturbation of the piezoelectric element in an ultrasonic transducer in a multimode fashion allows for generation of a multidimensional acoustic standing wave. A piezoelectric element can be specifically designed to deform in a multi-mode fashion at designed frequencies, allowing for generation of a multi-dimensional acoustic standing wave. The multi-dimensional acoustic standing wave may be generated by distinct modes of the piezoelectric element such as the 3×3 mode that would generate multidimensional acoustic standing waves. A multitude of multidimensional acoustic standing waves may also be generated by allowing the piezoelectric element to vibrate through many different mode shapes. Thus, the piezoelectric element would excite multiple modes such as a 0×0 mode (i.e. a piston mode) to a 1×1, 2×2, 1×3, 3×1, 3×3, and other higher order modes and then cycle back through the lower modes of the piezoelectric element (not necessarily in straight order), or the excitation may be a weighted combination of several modes. This switching or dithering of the piezoelectric element between modes allows for various multidimensional wave shapes, along with a single piston mode shape to be generated over a designated time.

It is also possible to drive multiple ultrasonic transducers with arbitrary phasing. In other words, the multiple transducers may work to separate materials in a fluid stream while being out of phase with each other. Alternatively, a single ultrasonic transducer that has been divided into an ordered array may also be operated such that some components of the array will be out of phase with other components of the array.

It may be necessary, at times, due to acoustic streaming, to modulate the frequency or voltage amplitude of the standing wave. This may be done by amplitude modulation and/or by frequency modulation. The duty cycle of the propagation of the standing wave may also be utilized to achieve certain results for trapping of materials. In other words, the acoustic beam may be turned on and shut off at different frequencies to achieve desired results.

The lateral force of the total acoustic radiation force (ARF) generated by the ultrasonic transducers of the present disclosure is significant and is sufficient to overcome the fluid drag force at high linear velocities up to 1 cm/s and beyond. For example, linear velocities through the devices of the present disclosure can be a minimum of 4 cm/min for separation of cells/particles, and can be as high as 1 cm/sec for separation of oil/water phases. This can be relevant when, as described further below, an ultrasonic transducer is moved relative to a standing volume of fluid to enhance separation.

If desired, multiple standing waves from multiple ultrasonic transducers can also be used, which allows for multiple separation stages. For example, in a mixture of particles and fluid, the first transducer (and its standing wave) will collect a certain amount of the particles, and the second transducer (and its standing wave) will collect additional particles that the first transducer was not able to hold. This construction can be useful where the particle/fluid ratio is high (i.e. large volume of particles), and the separation capacity of the first transducer is reached. This construction can also be useful for particles that have a bimodal or greater size distribution, where each transducer can be optimized to capture particles within a certain size range.

FIG. 1 illustrates a first exemplary embodiment of an acoustophoretic device 100 of the present disclosure to be used with a discrete volume of fluid medium. This fluid may be considered to be non-flowing, in that there is no pump moving the fluid, and there is no additional fluid being added to this discrete volume or displaced from this discrete volume. The acoustophoretic device includes a substantially acoustically transparent container 110 and a separation unit 120. These two components are separable from each other.

The container 110 of the acoustophoretic device is generally formed from a substantially acoustically transparent material such as plastic, glass, polycarbonate, low-density polyethylene, and high-density polyethylene (all at an appropriate thickness). However, the container may be formed from any material suitable for allowing the passage of the acoustic standing wave(s) of the present disclosure therethrough. The container may be in the form of a bottle or a bag or a cell that fits in the separation unit. The difference between these forms lies in their composition and structure. A bottle is more rigid than a bag. When empty, a bag is generally unable to support itself, while a bottle is able to stand upright. For example, container 110 as shown in FIG. 1 is a high-density polyethylene bag. Container 110 generally has an upper end 112 and a lower end 114, and an interior volume in which the non-flowing fluid medium is located. This fluid medium is a mixture of a host fluid which is a majority of the fluid medium, and a second fluid or particulate which is dispersed in the host fluid.

The separation unit 120 of the acoustophoretic device is defined by at least one wall 122, and may have a plurality of walls, which form the side of the separation unit. For example, the separation unit may be in the shape of a cylinder, or in a rectangle (as depicted). The wall(s) are solid. An opening 126 is present in an upper end of the separation unit, for receiving the container 110 therethrough. Again, the separation unit 120 is separable from the container 110, so that the container can be either disposable or reusable, depending upon the desired application of the acoustophoretic device. As illustrated here, the base of the separation unit 120 is solid.

The separation unit 120 includes at least one ultrasonic transducer 130 on a wall 134. The ultrasonic transducer 130 has a piezoelectric element driven by a voltage signal to create an acoustic standing wave. Cables 132 are illustrated for transmitting power and control information to the ultrasonic transducer 130. A reflector 140 may be present, and is located on the wall 136 opposite the ultrasonic transducer 130. The standing wave is thus generated through initial waves radiated from the transducer and reflected waves from the reflector. In some embodiments, a reflector is not necessary and, rather, ambient air may be used to reflect the incident waves and create the standing waves. It is to be understood that various transducer and reflector combinations may be utilized for the creation of acoustic standing wave(s) of the present disclosure to accelerate the gravity settling of particles or the buoyancy rising of particles or low-density fluids, respectively, that are disposed within the non-flowing fluid medium. The planar and/or multi-dimensional acoustic standing wave(s) are generated within the container, and are used to increase the speed of settling of particles in a non-flowing fluid in the container. This process may also be utilized in a batch or semi-batch operation where the particle and fluid mixture may be stopped for a period of time while the acoustic standing wave is used to accelerate the separation of particles in the fluid before resuming introduction of the fluid with the particles now separated to the bottom of a well or catch area. It should be noted that there is no contact between the ultrasonic transducer and the discrete volume of fluid that is being separated.

In certain embodiments, the acoustophoretic device includes a plurality of ultrasonic transducers 130 located on a common wall 134 of the separation unit opposite the wall 136 on which the reflector 140 is located. Alternatively, the ultrasonic transducers can be located opposite each other, with no reflector being present. Additionally, the separation unit 120 may include a viewing window 124 in another wall 138 of the separation unit 120. As shown in the embodiment of FIG. 1, when a viewing window is provided, it can be in a wall of the separation unit adjacent the walls upon which the ultrasonic transducer(s) and reflector are located, such that the lower end 114 of the container 110 can be viewed through the viewing window 124 in the separation chamber 120. In other embodiments, the viewing window can take the place of the reflector.

In certain embodiments, a fluid, such as water, may be placed in the interstitial space 105 between the container 110 and the separation unit 120, such that the acoustic standing wave passes through both the fluid in the separation unit and the non-flowing fluid medium in the container. The interstitial fluid can be any fluid, though it is desirable to use fluid with acoustic properties similar to the discrete volume of fluid in the container, so as not to prevent the acoustic standing wave(s) from passing through the non-flowing fluid medium in the container for separation and clarification therein. The fluid in the interstitial space should have an acoustic impedance value that allows for good transmission of the acoustic standing wave(s), and preferably a low acoustic attenuation.

In certain embodiments, the separation unit 120 includes a support structure that is configured to move the ultrasonic transducer(s) 130 vertically relative to the container 110, along with the reflector 140 when present. The movement of the transducer creates a "sweeping effect" through the non-flowing fluid mixture in the container 110 from the upper end 112 to the lower end 114 or from the lower end 114 to the upper end 112 thereof, depending on the direction of the vertical movement. This "sweeping" of the fluid in the container improves the settling or buoyancy of particles that are disposed within the fluid. The ultrasonic transducer may be moved relative to the container at a linear velocity of from about 0.1 millimeter/second to about 1 centimeter/second.

Figure 2:
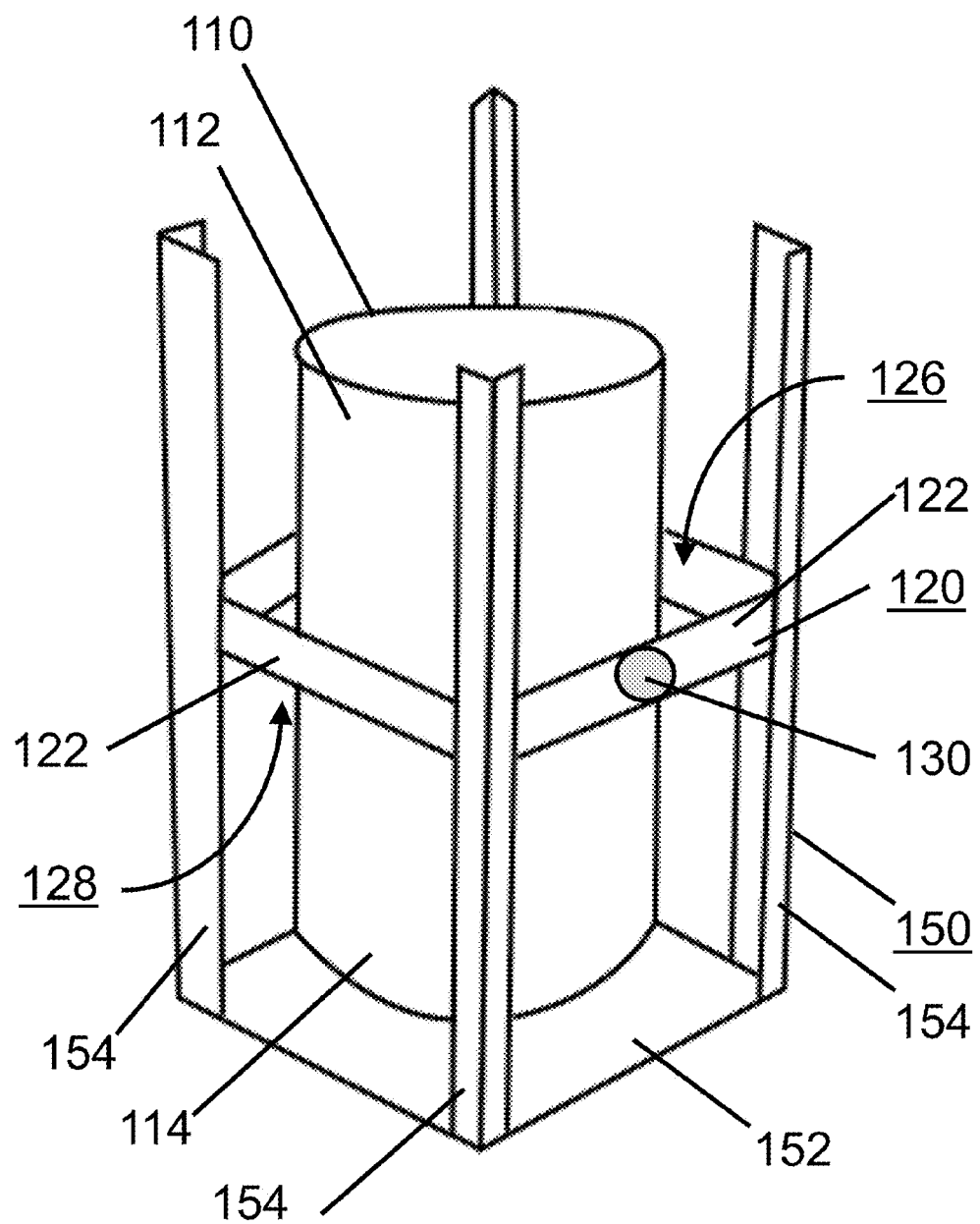
FIG. 2 is a cross-sectional view of another exemplary embodiment of an acoustophoretic device of the present disclosure, including a support structure for moving the separation unit relative to the container.

One such device is depicted in FIG. 2. Here, the separation unit 120 is made up of four walls 122, with the transducer 130 on one of the walls (reflector not visible). The unit 120 includes an upper opening 126 and a lower opening 128, with the container 110 passing through both openings. The support structure 150 here includes a base 152 and support pillars 154 rising vertically from the base. The support pillars provide a mechanism for moving the separation unit 120 up and down relative to the container 110, which maintains its position on the base. The mechanism can be any known in the art, e.g. gears, pulleys, etc. The separation unit 120 is depicted here at roughly the middle of the container 110, and arrows indicate that the separation unit 120 can move upwards or downwards as desired. For example, the transducer 130 can be moved is moved from the upper end 112 towards the lower end 114 of the container 110 so as to enhance the settling of the particles at the bottom of the container. Alternatively, the transducer 130 could be raised from the lower end 114 of the container towards the upper end 112 of the container 110 so as to increase the separation of buoyant particles, such as in an oil-water mixture where the oil is being separated from the water.

Figure 3:
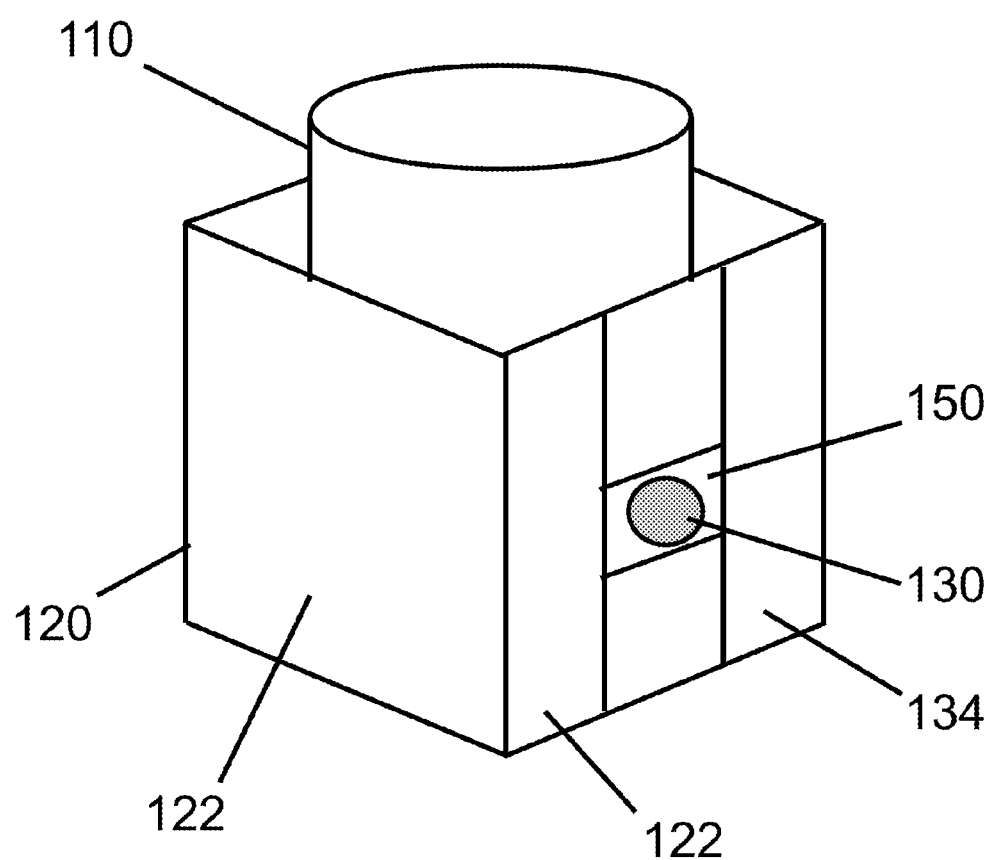
FIG. 3 is a perspective view of another exemplary acoustophoretic device of the present disclosure with a support structure. Here, the separation unit contains the support structure within its walls, and the support structure only translates the ultrasonic transducer/reflector pair along an axis, while the walls of the separation unit remain in a static location relative to the container.

Another embodiment of such a device is present in FIG. 3. Here, the ultrasonic transducer 130 is mounted on a support structure 150 within the separation unit 120, and the wall 134 includes a track along which the support structure moves vertically relative to the container 110. The walls 122 of the separation unit 120 do not move relative to the container 110, only the transducer (and reflector if present).

The various parts of the acoustophoretic devices of this disclosure can be made from any suitable material. Such suitable materials include medical grade plastics, such as polycarbonates or polymethyl methacrylates, or other acrylates, metals such as steel, or glass. It is generally desirable for the material to be somewhat transparent, so that a clear window can be produced and the internal flow channels and flow paths can be seen during operation of the acoustophoresis device/system.

Some explanation of the ultrasonic transducers used in the devices of the present disclosure may be helpful as well. In this regard, the transducers use a piezoelectric element, usually made of PZT-8 (lead zirconate titanate). Such elements may have a 1 inch diameter and a nominal 2 MHz resonance frequency, or may be of a square or rectangular shape. Each ultrasonic transducer module can have only one piezoelectric element, or can have multiple piezoelectric elements that each act as a separate ultrasonic transducer and are either controlled by one or multiple amplifiers.

FIG. 4 is a cross-sectional diagram of a conventional ultrasonic transducer. This transducer has a wear plate 50 at a bottom end, epoxy layer 52, ceramic piezoelectric element 54 (made of, e.g. PZT), an epoxy layer 56, and a backing layer 58. On either side of the ceramic piezoelectric element, there is an electrode: a positive electrode 61 and a negative electrode 63. The epoxy layer 56 attaches backing layer 58 to the piezoelectric element 54. The entire assembly is contained in a housing 60 which may be made out of, for example, aluminum. An electrical adapter 62 provides connection for wires to pass through the housing and connect to leads (not shown) which attach to the piezoelectric element 54. Typically, backing layers are designed to add damping and to create a broadband transducer with uniform displacement across a wide range of frequency and are designed to suppress excitation at particular vibrational eigen-modes. Wear plates are usually designed as impedance transformers to better match the characteristic impedance of the medium into which the transducer radiates.

Figure 5:
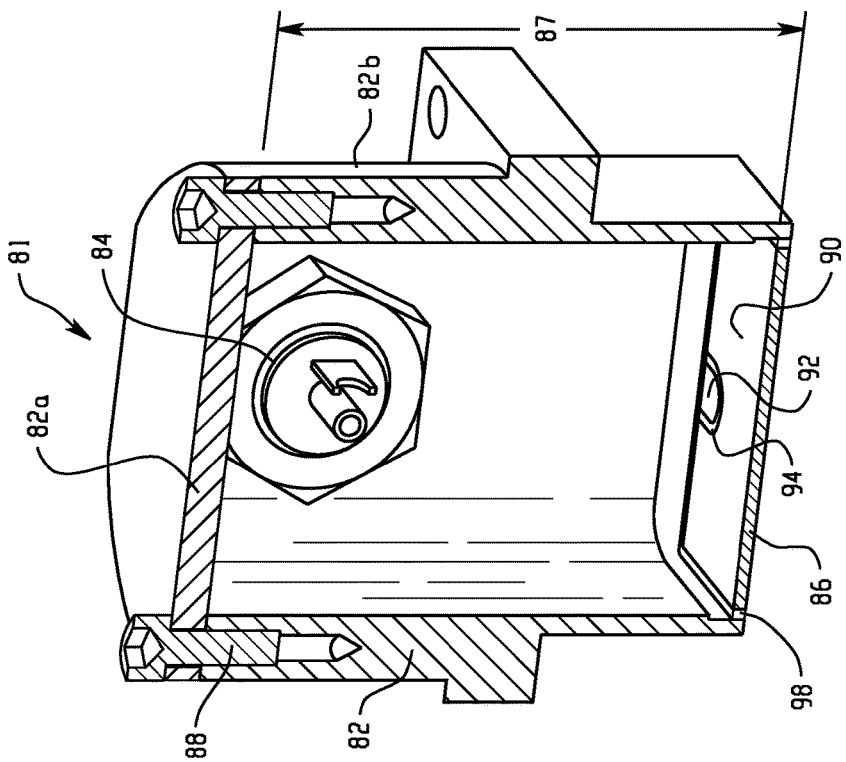
FIG. 5 is a cross-sectional diagram of an ultrasonic transducer of the present disclosure. An air gap is present within the transducer, and no backing layer or wear plate is present.

FIG. 5 is a cross-sectional view of an ultrasonic transducer 81 of the present disclosure. Transducer 81 is shaped as a square, and has an aluminum housing 82. The piezoelectric element is a mass of perovskite ceramic, each consisting of a small, tetravalent metal ion, usually titanium or zirconium, in a lattice of larger, divalent metal ions, usually lead or barium, and $O^{2-}$ ions. As an example, a PZT (lead zirconate titanate) piezoelectric element 86 defines the bottom end of the transducer, and is exposed from the exterior of the housing. The piezoelectric element is supported on its perimeter by a small elastic layer 98, e.g. epoxy, silicone or similar material, located between the piezoelectric element and the housing. Put another way, no wear plate is present. However, in some embodiments, there is a layer of plastic or other material separating the piezoelectric element from the fluid in which the acoustic standing wave is being generated.

Figure 6:
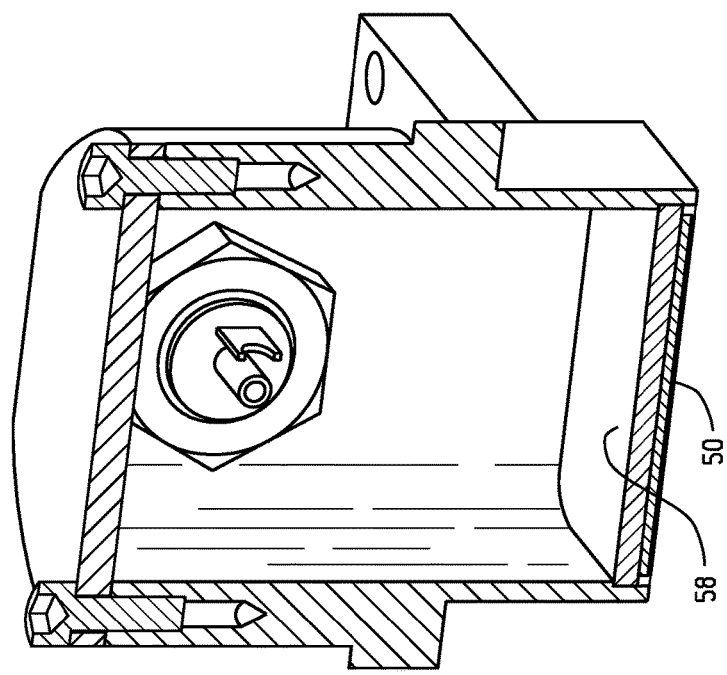
FIG. 6 is a cross-sectional diagram of an ultrasonic transducer of the present disclosure. An air gap is present within the transducer, and a backing layer and wear plate are present.

Screws 88 attach an aluminum top plate 82a of the housing to the body 82b of the housing via threads. The top plate includes a connector 84 for powering the transducer. The top surface of the PZT piezoelectric element 86 is connected to a positive electrode 90 and a negative electrode 92, which are separated by an insulating material 94. The electrodes can be made from any conductive material, such as silver or nickel. Electrical power is provided to the PZT piezoelectric element 86 through the electrodes on the piezoelectric element. Note that the piezoelectric element 86 has no backing layer or epoxy layer. Put another way, there is an air gap 87 in the transducer between aluminum top plate 82a and the piezoelectric element 86 (i.e. the air gap is completely empty). A minimal backing 58 and/or wear plate 50 may be provided in some embodiments, as seen in FIG. 6.

The transducer design can affect performance of the system. A typical transducer is a layered structure with the ceramic piezoelectric element bonded to a backing layer and a wear plate. Because the transducer is loaded with the high mechanical impedance presented by the standing wave, the traditional design guidelines for wear plates, e.g., half wavelength thickness for standing wave applications or quarter wavelength thickness for radiation applications, and manufacturing methods may not be appropriate. Rather, in one embodiment of the present disclosure the transducers, there is no wear plate or backing, allowing the piezoelectric element to vibrate in one of its eigenmodes (i.e. near eigenfrequency) with a high Q-factor. The vibrating ceramic piezoelectric element is directly exposed to the fluid flowing through the flow chamber.

Removing the backing (e.g. making the piezoelectric element air backed) also permits the ceramic piezoelectric element to vibrate at higher order modes of vibration with little damping (e.g. higher order modal displacement). In a transducer having a piezoelectric element with a backing, the piezoelectric element vibrates with a more uniform displacement, like a piston. Removing the backing allows the piezoelectric element to vibrate in a non-uniform displacement mode. The higher order the mode shape of the piezoelectric element, the more nodal lines the piezoelectric element has. The higher order modal displacement of the piezoelectric element creates more trapping lines, although the correlation of trapping line to node is not necessarily one to one, and driving the piezoelectric element at a higher frequency will not necessarily produce more trapping lines.

In some embodiments, the piezoelectric element may have a backing that minimally affects the Q-factor of the piezoelectric element (e.g. less than 5%). The backing may be made of a substantially acoustically transparent material such as balsa wood, foam, or cork which allows the piezoelectric element to vibrate in a higher order mode shape and maintains a high Q-factor while still providing some mechanical support for the piezoelectric element. The backing layer may be a solid, or may be a lattice having holes through the layer, such that the lattice follows the nodes of the vibrating piezoelectric element in a particular higher order vibration mode, providing support at node locations while allowing the rest of the piezoelectric element to vibrate freely. The goal of the lattice work or acoustically transparent material is to provide support without lowering the Q-factor of the piezoelectric element or interfering with the excitation of a particular mode shape.

Figure 7:
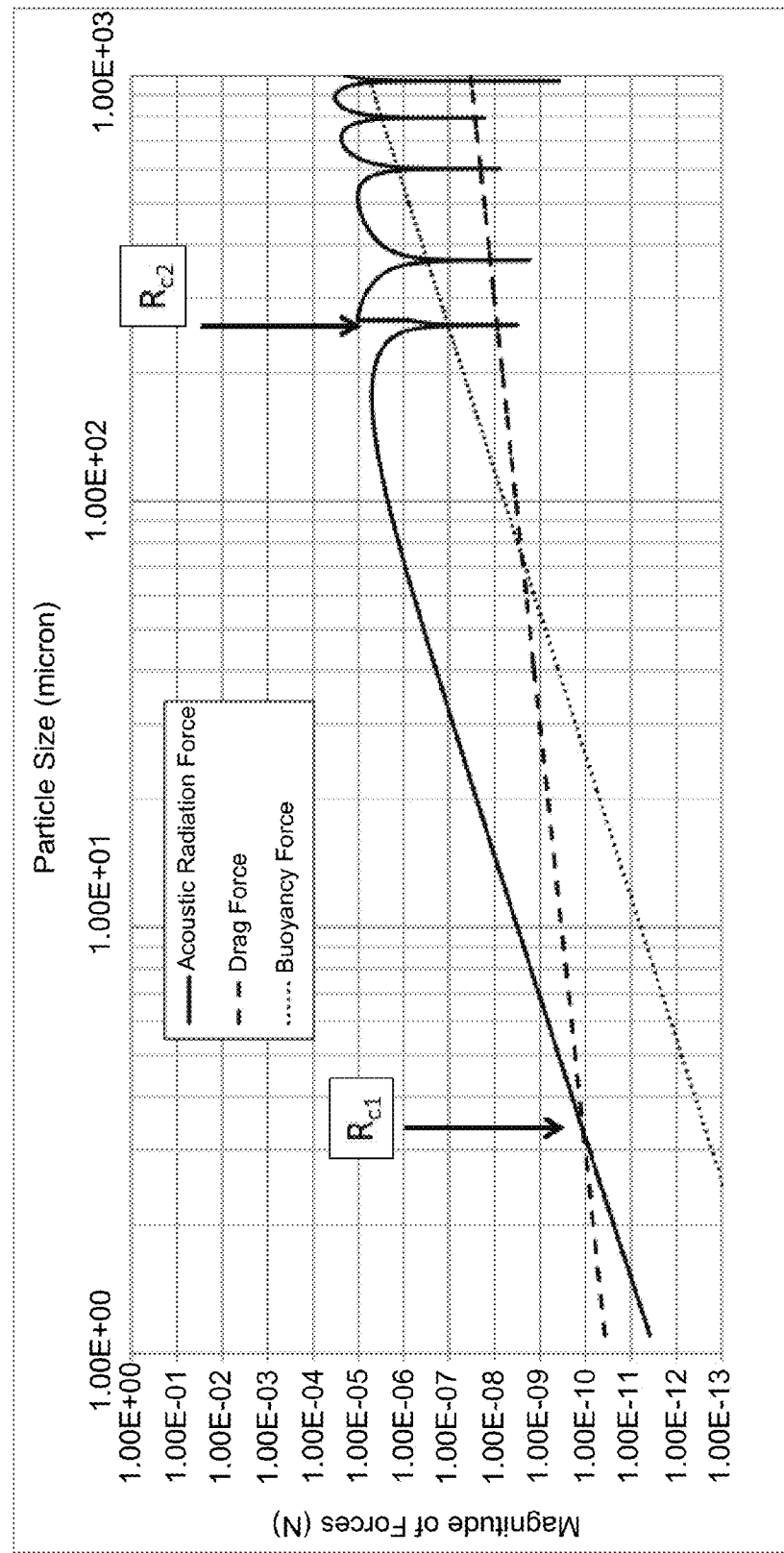
FIG. 7 is a graph showing the relationship of the acoustic radiation force, gravity/buoyancy force, and Stokes' drag force to particle size. The horizontal axis is in microns (µm) and the vertical axis is in Newtons (N).

FIG. 7 is a log-log graph (logarithmic y-axis, logarithmic x-axis) that shows the scaling of the acoustic radiation force, fluid drag force, and buoyancy force with particle radius, and provides an explanation for the separation of particles using acoustic radiation forces. Calculations are done for a typical CHO cell used in experiments. The buoyancy force is a particle volume dependent force, and is therefore negligible for particle sizes on the order of micron, but grows, and becomes significant for particle sizes on the order of hundreds of microns. The fluid drag force (Stokes drag force) scales linearly with the velocity (when the transducer is moving relative to the non-flowing fluid in the container), and therefore typically exceeds the buoyancy force for micron sized particles, but is negligible for larger sized particles on the order of hundreds of microns. The acoustic radiation force scaling is different. When the particle size is small, Gor'kov's equation is accurate and the acoustic trapping force scales with the volume of the particle. Eventually, when the particle size grows, the acoustic radiation force no longer increases with the cube of the particle radius, and will rapidly vanish at a certain critical particle size. For further increases of particle size, the radiation force increases again in magnitude but with opposite phase (not shown in the graph). This pattern repeats for increasing particle sizes.

Initially, when the container includes a host fluid with primarily small micron sized particles and the transducer is moving relative to the container, it is necessary for the acoustic radiation force to balance the combined effect of fluid drag force and buoyancy force for a particle to be trapped in the standing wave. In FIG. 7 this happens for a particle size of about 3.5 micron, labeled as $R_{c1}$. The graph then indicates that all larger particles will be trapped as well. Therefore, when small particles are trapped in the standing wave, particles coalescence/clumping/aggregation/agglomeration takes place, resulting in continuous growth of effective particle size. As particles cluster, the total drag on all of the particles in the cluster is much lower than the sum of the drag forces on the individual particles. In essence, as the particles cluster, they reduce the overall drag of the cluster. As the particle size grows, the acoustic radiation force reflects off the particle, such that large particles will cause the acoustic radiation force to decrease. The acoustic lateral forces on the particles must be larger than the drag forces for the clusters to remain stationary and grow in size.

Particle size growth continues until the gravity/buoyancy force becomes dominant, which is indicated by a second critical particle size, $R_{c2}$, at which size the particles will rise or sink, depending on their relative density with respect to the host fluid. At this size, acoustic forces are secondary, gravity/buoyancy forces become dominant, and the particles naturally drop out of the host fluid. Not all particles will drop out, and those remaining particles will continue to grow in size as well. This phenomenon explains the quick drops and rises in the acoustic radiation force beyond size $R_{c2}$. Thus, FIG. 7 explains how small particles can be trapped continuously in a standing wave, grow into larger particles or clumps, and then eventually will rise or settle out because of increased buoyancy force or gravity. In the absence of transducer motion, the drag force is then solely due to the motion of the particle in the fluid, and will be smaller compared to the case of transducer motion, i.e., Rc1 will be smaller and hence smaller particle sizes can be trapped for a stationary transducer operation.

The size, shape, and thickness of the transducer determine the transducer displacement at different frequencies of excitation, which in turn affects particle separation efficiency. Typically, the transducer is operated at frequencies near the thickness resonance frequency (half wavelength). Gradients in transducer displacement typically result in more places for particles to be trapped. Higher order modal displacements generate three-dimensional acoustic standing waves with strong gradients in the acoustic field in all directions, thereby creating equally strong acoustic radiation forces in all directions, leading to multiple trapping lines, where the number of trapping lines correlate with the particular mode shape of the transducer.

Figure 8:
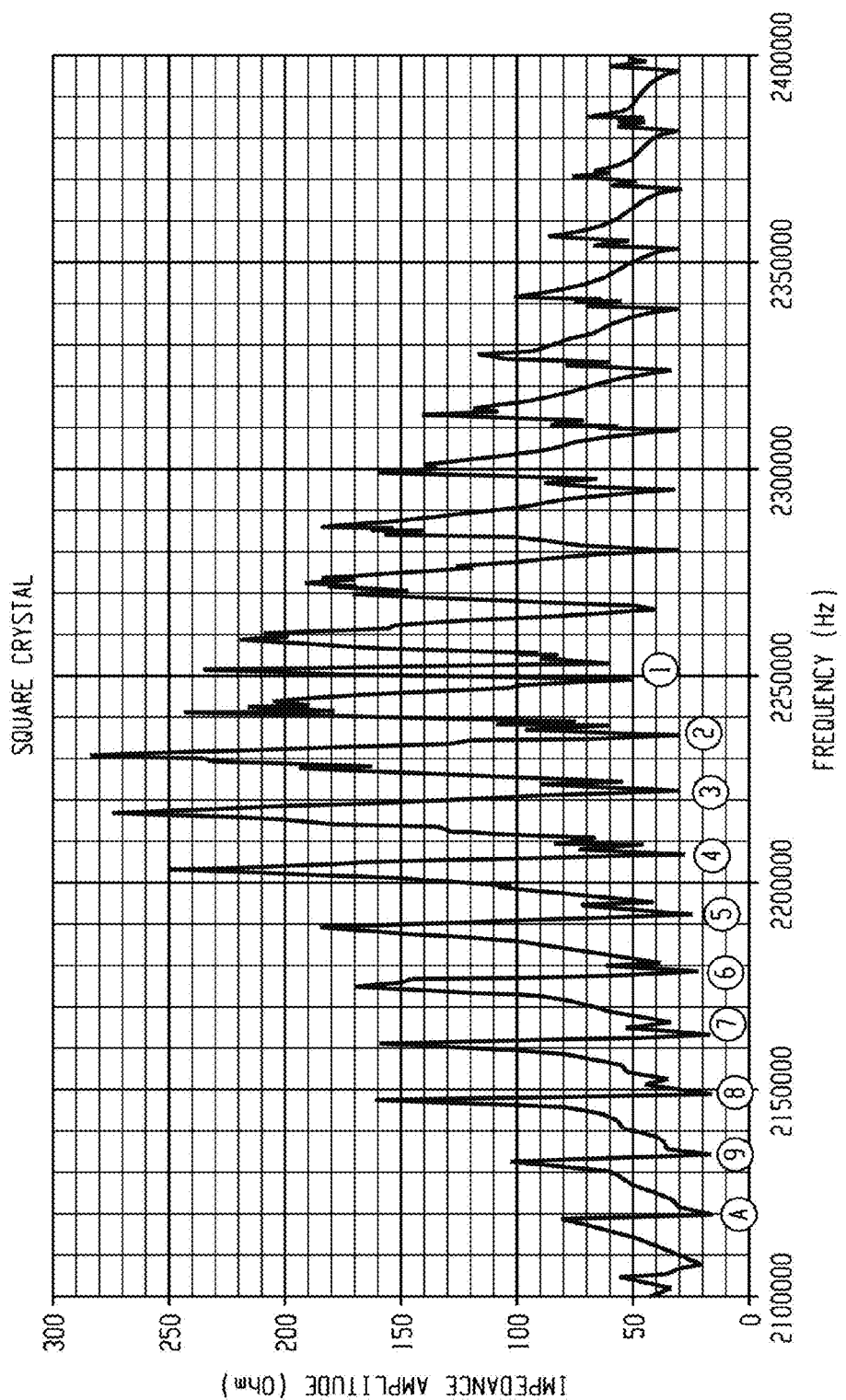
FIG. 8 is a graph of electrical impedance amplitude versus frequency for a square transducer driven at different frequencies.

FIG. 8 shows the measured electrical impedance amplitude of the transducer as a function of frequency in the vicinity of the 2.2 MHz transducer resonance. The minima in the transducer electrical impedance correspond to acoustic resonances of a water column and represent potential frequencies for operation. Numerical modeling has indicated that the transducer displacement profile varies significantly at these acoustic resonance frequencies, and thereby directly affects the acoustic standing wave and resulting trapping force. Since the transducer operates near its thickness resonance, the displacements of the electrode surfaces are essentially out of phase. The typical displacement of the transducer electrodes is not uniform and varies depending on frequency of excitation. As an example, at one frequency of excitation with a single line of trapped particles, the displacement has a single maximum in the middle of the electrode and minima near the transducer edges. At another excitation frequency, the transducer profile has multiple maxima leading to multiple trapped lines of particles. Higher order transducer displacement patterns result in higher trapping forces and multiple stable trapping lines for the captured particles.

To investigate the effect of the transducer displacement profile on acoustic trapping force and particle separation efficiencies, an experiment was repeated ten times, with all conditions identical except for the excitation frequency. Ten consecutive acoustic resonance frequencies, indicated by circled numbers 1-9 and letter A on FIG. 8, were used as excitation frequencies. The conditions were experiment duration of 30 min, a 1000 ppm oil concentration of approximately 5-micron SAE-30 oil droplets, a flow rate of 500 ml/min, and an applied power of 20 W.

Figure 9A:
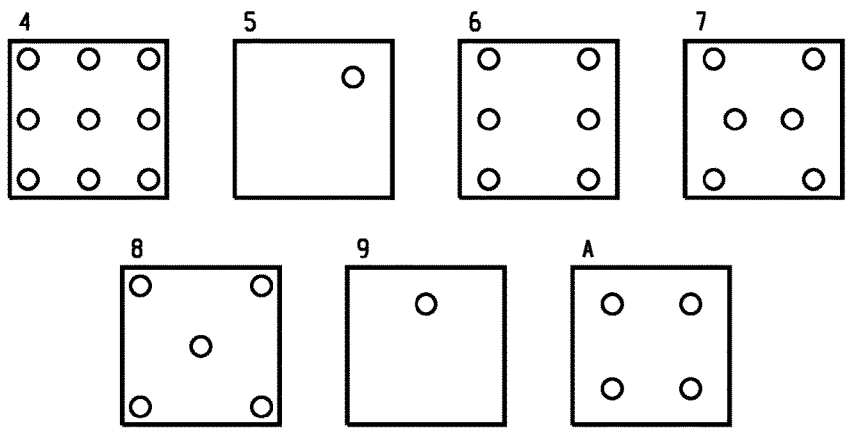
FIG. 9A illustrates the trapping line configurations for seven of the peak amplitudes of FIG. 8 from the direction orthogonal to fluid flow.

As the emulsion passed by the transducer, the trapping lines of oil droplets were observed and characterized. The characterization involved the observation and pattern of the number of trapping lines across the fluid channel, as shown in FIG. 9A, for seven of the ten resonance frequencies identified in FIG. 8.

Figure 9B:
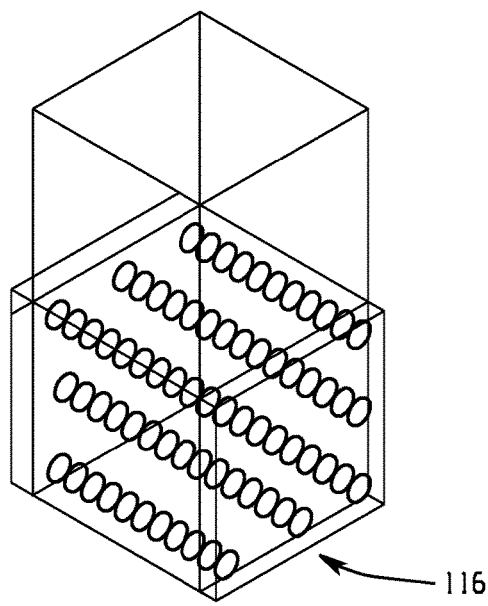
FIG. 9B is a perspective view illustrating the separator. The trapping lines are shown.
Figure 9C:
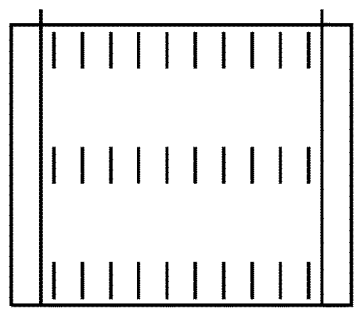
FIG. 9C is a view from the side of the separator, normal to the transducer of FIG. 9B, showing the trapping nodes of the standing wave where particles would be captured.
Figure 9D:
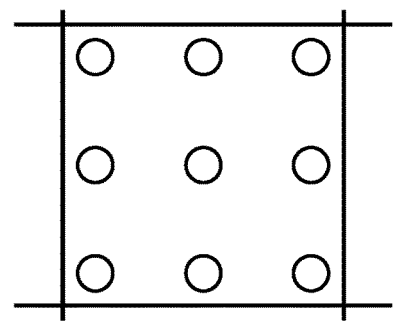
FIG. 9D is a view taken through the face of the transducer showing the trapping line configurations, along arrow 116 as shown in FIG. 9B.

FIG. 9B shows an isometric view of a system of the present disclosure where the trapping line locations are indicated. FIG. 9C is a view of the system as it appears from the side, looking at the trapping lines. FIG. 9D is a view of the system as it appears when looking directly at the transducer face, along arrow 116.

The effect of excitation frequency clearly determines the number of trapping lines, which vary from a single trapping line at the excitation frequency of acoustic resonance 5 and 9, to nine trapping lines for acoustic resonance frequency 4. At other excitation frequencies four or five trapping lines are observed. Different displacement profiles of the transducer can produce different (more) trapping lines in the standing waves, with more gradients in displacement profile generally creating higher trapping forces and more trapping lines.

In the present systems, the system is operated at a voltage such that the particles and particle clusters are trapped in the ultrasonic standing wave. The particles and clusters are collected in well-defined trapping lines. Each trapping line is aligned with the main direction of the acoustic standing wave. Particles and clusters in the trapping lines are separated by half a wavelength. Within each pressure nodal plane of the standing wave, the particles are trapped at very specific points, typically the minima of the acoustic radiation potential. The axial component of the acoustic radiation force drives the particles, with a positive contrast factor, to the pressure nodal planes, whereas particles with a negative contrast factor are driven to the pressure anti-nodal planes. The radial or lateral component of the acoustic radiation force is the force that traps the particles in the standing wave, clumps or clusters them into tightly packed clusters, which then gravity separate when the clusters reach a critical size. In systems using typical transducers, the radial or lateral component of the acoustic radiation force is typically several orders of magnitude smaller than the axial component of the acoustic radiation force. It therefore has two limitations. It has very weak trapping capabilities of particles and moreover, it cannot generate tightly enough packed clusters that will separate out due to gravity. The lateral force in the present devices can be significant, on the same order of magnitude as the axial force component. The strong clustering capability leads to rapid formation of clusters which continuously separate out from the host fluid through gravity/buoyancy separation.

The three-dimensional acoustic standing waves are the result of superposition of the vibration modes of the piezoelectric element. The three dimensional force field results in strong gradients within every nodal plane of the standing wave. Multiple particle clusters are formed along a line in the axial direction of the standing wave, as illustrated in FIG. 9B. For optimum collection, the shape of the particle clusters should give the lowest drag. At particle Reynolds numbers below 20, cylindrical shapes have significantly lower drag coefficients than spheres. Cylinders can also carry significantly more particles (mass) for a given surface area, so that a cylindrical particle cluster will have higher gravity/buoyancy forces and lower resistance drag than a spherical particle cluster. Thus a cylindrical particle cluster will drop out faster than other shapes. It is noted that "cylinder" is used as a shorthand for describing the shape of such clusters, which may perhaps be better described as being ellipsoidal.

Referring back to FIG. 1, the overall system thus operates as follows. One or more acoustic standing waves are created between the transducer 130 and the reflector 140 of the separation unit 120; these waves also pass through the container 110. Particles present in the fluid/particle mixture in the container 110 are trapped in acoustic standing waves at the pressure nodes for particles with positive acoustic contrast and at the pressure anti-nodes for particles with negative acoustic contrast, where they agglomerate, aggregate, clump, or coalesce into larger clusters of particles. The clusters then either rise or sink and are separated from the fluid, which as a result is clarified. Gravity driven flows are present in the system which further enhance the clarification. When clumps of particles settle, an equal volume of lighter and clarified fluid is displaced from the region of the bottom and moves to the top.

Figure 11:
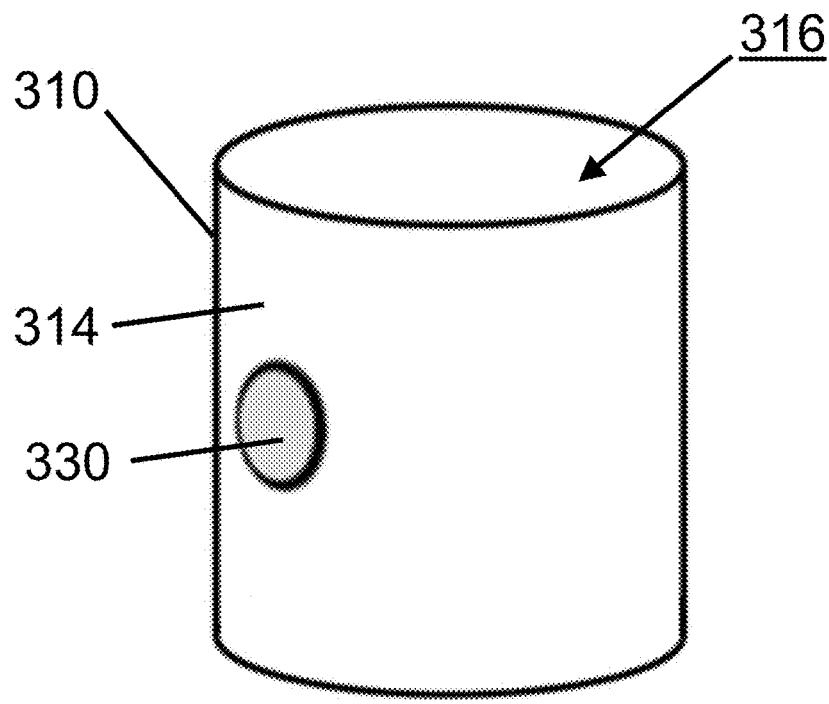
FIG. 11 is a schematic diagram of another exemplary acoustophoretic device of the present disclosure. A disposable flexible plastic bag contains an embedded ultrasonic transducer.
Figure 12:
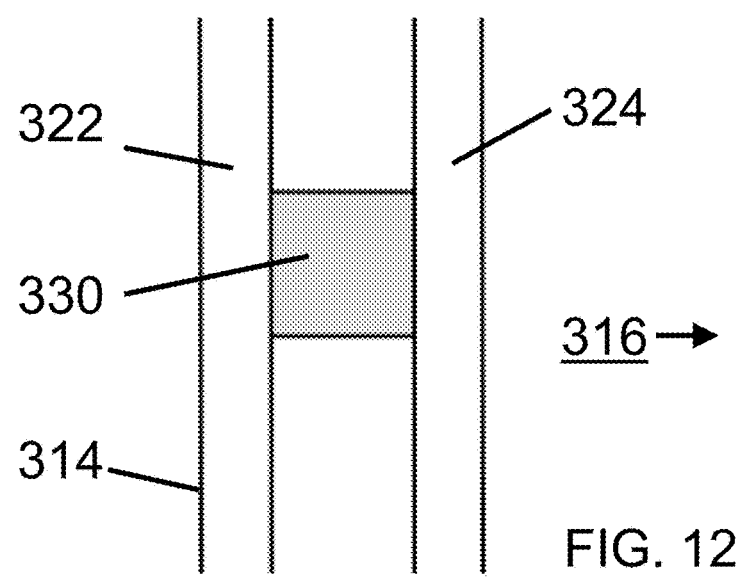
FIG. 12 is a cross-sectional diagram of the bag of FIG. 11, showing the transducer embedded within the bag.

FIG. 11 and FIG. 12 illustrate another embodiment of an acoustophoretic device in accordance with the present disclosure. FIG. 11 is an exterior view of the bag, and FIG. 12 is a cross-sectional view of the bag. In this embodiment, the acoustophoretic device generally includes a disposable separation bag 310. The disposable separation bag 310 includes an exterior surface 314 and an interior volume 316 bounded by the exterior surface 314. The disposable separation bag 310 may be made from at least one polymer layer (e.g., polyethylene, polyurethane, polypropylene, and the like). It is also contemplated that the bag can be made from multiple layers of differentially functioning polymer layers. Those polymer layers may function as a waterproof layer, as a layer that provides strength, etc. For example, in some instances, the exterior (i.e. outermost layer) of the bag is a polyethylene terephthalate (PET) polymer. A middle or central layer of the bag can be typically ethylene vinyl alcohol (EVOH) or polyvinyl acetate (PVA). The interior layer (contacting the bioreactor cell culture medium) is typically a polyethylene polypropylene such as low-density polyethylene or very low density polyethylene. The bag has a large interior volume, generally of at least one liter, up to 1000 liters, and even larger as desired.

An ultrasonic transducer 330 is at least partially disposed inward of the exterior surface 314 of the separation bag 310, such that an acoustic standing wave can be created in the interior volume 316 of the bag. The ultrasonic transducer 330 includes a piezoelectric element driven by a voltage signal to create the acoustic standing wave. As illustrated in FIG. 12, the ultrasonic transducer 330 is between two polymeric layers 322, 324 (please note that the two layers are joined together, and there is no free space between them—this is an artifact of the drawing). The ultrasonic transducer and the acoustic standing wave are the same as described with reference to the various other embodiments disclosed herein. That is, the acoustic standing wave field is created by the ultrasonic transducer 330 within the interior volume 316 of the disposable separation bag 310 such that particles disposed within the fluid can coalesce or agglomerate and drop below or rise above the acoustic standing wave field due to gravitational or buoyancy forces. Put another way, this embodiment allows for a disposable system whereby solids disposed within the fluid in the bag may be agglomerated and drop out of solution above or below the acoustic standing wave field due to gravitational/buoyancy forces and the acoustic standing wave field, thereby resulting in clarification of the fluid in the bag. Here, the reflector is the air that is on the opposite side of the bag from the ultrasonic transducer. This bag is not used with the separation unit 120 of FIG. 1.

Various types of plastics can be used to form the container of the present disclosure. Matching the impedance value of the plastic chosen is important and will depend upon the frequency at which the ultrasonic transducer(s) is driven to generate the planar, multi-dimensional, or combination acoustic standing wave. Thus, it is contemplated that the containers or separation bags disclosed herein may be formed of one or more of the materials of Table 1, depending on the desired characteristics of the containers or separation bags and the desired frequency at which the ultrasonic transducer(s) are to be driven for the non-flow separation and clarification of the fluid.

Table 1 below shows the impedance values for various types of plastics. The values in Table 1 are Vl=longitudinal sound velocity (m/s); D=density (g/cm³); and Z=acoustic impedance (Megarayls).

TABLE 1

Impedance Values for Various Plastics

| Material | Vl | D | Z |
|---|---|---|---|
| ABS | 2,230 | 1.03 | 2.31 |
| Acrylic Plexiglas | 2,750 | 1.19 | 3.26 |
| Adiprene | 1,689 | 1.16 | 1.94 |
| Bakelite | 1,590 | 1.40 | 3.63 |
| Cellulose Butyrate | 2,140 | 1.19 | 2.56 |
| Delrin | 2,430 | 1.42 | 3.45 |
| EPO-TEK 301 | 2,640 | 1.08 | 2.85 |
| Ethyl Vinyl Acetate | 1,800 | 0.94 | 1.69 |
| Neoprene | 1,600 | 1.31 | 2.10 |
| Mylar | 2,450 | 1.18 | 3.00 |
| Nylon 6/6 | 2,600 | 1.12 | 2.90 |
| Polycarbonate | 2,270 | 1.22 | 2.77 |
| Polyester Casting Resin | 2,290 | 1.07 | 2.86 |
| Polyethylene | 1,950 | 0.90 | 1.76 |
| Polyethylene (high-density) | 2,430 | 0.96 | 2.33 |
| Polyethylene (low-density) | 1,950 | 0.92 | 1.79 |
| Polypropylene | 2,470 | 0.88 | 2.40 |
| Polystyrene | 2,320 | 1.04 | 2.42 |
| Polyurethane | 1,700 | 1.04 | 1.80 |
| PVC | 2,380 | 1.38 | 3.27 |
| PVDF | 2,300 | 1.79 | 4.20 |
| Scotch Tape (2.5 mm thick) | 1,900 | 1.16 | 2.08 |
| Vinyl (rigid) | 2,230 | 1.33 | 2.96 |

In biological applications, it is contemplated that all of the parts of the system (i.e., the container, separation unit, etc.) can be separated from each other and be disposable. Avoiding centrifuges and filters allows better separation of the fluid from particles disposed therein without lowering the viability of the particles. The transducers may also be driven to create rapid pressure changes to prevent or clear blockages due to agglomeration of the particles. The frequency of the transducers may also be varied to obtain optimal effectiveness for a given power.

The following examples are provided to illustrate the devices, components, and methods of the present disclosure. The examples are merely illustrative and are not intended to limit the disclosure to the materials, conditions, or process parameters set forth therein.

EXAMPLES

FIG. 10 shows an experimental setup for an acoustophoretic device as described in detail above. This acoustophoretic device is very similar to that illustrated in FIG. 1, except the container is a volumetric plastic bag. The lower end of the plastic bag is disposed within the walls of the separation unit and the separation unit includes an ultrasonic transducer and reflector. The ultrasonic transducer is driven by a voltage signal provided by a BNC cable. An acoustic standing wave is generated by the ultrasonic transducer through the separation unit and lower end of the container for clarifying the fluid contained therein.

The clarification and separation process was conducted where the volumetric plastic bag was filled with a non-flowing fluid medium, namely a fluid and yeast mixture. In accordance with the previously described process, the bag containing the fluid mixture was placed into the separation unit with the bag situated between the transducer and the reflector of the separation unit such that the acoustic standing wave passed through both the plastic bag and the fluid mixture. The fluid contained yeast at a 6% concentration in a 1000 mL volume. The mixture had a starting NTU (Nephelometric Turbidity Units) of 11,800 and, after the above-described separation and clarification process using the devices and components described herein, the upper clarified layer had a final NTU of 856, demonstrating the effectiveness of clarifying a non-flowing mixture of fluid and yeast cells or static environment using acoustophoresis. This evidences that clarification of the fluid is occurring as the yeast cells coalesce or agglomerate in the acoustic standing wave and sink to the lower end of the container due to gravitational forces.

The parameters for the tests are shown in Table 2 below. Table 2 shows clarification results for a 6% yeast solution in water that was separated for 40 minutes using piezoelectric ultrasonic transducers excited at 2.2196 MHz and 2.2147 MHz. The feed is the starting mixture, in which the yeast is dispersed. The permeate is the clarified fluid at the top of the bag, and contains a lower concentration of particulate compared to the feed. The concentrate is the fluid at the bottom of the bag, and contains a higher concentration of particulate compared to the feed.

TABLE 2

Clarification results for a 6% yeast solution in water

| 6% yeast solution in water | Volume (mL) | Duration (minutes) | Frequency Top-Top (MHZ) | Frequency Top-Bottom (MHZ) |
|---|---|---|---|---|
| | 1,000 | 40 | 2.2196 | 2.2147 |
| | NTU Feed 11,800 | NTU Permeate 856 | NTU Concentrate 100,200 | PCV Concentrate — |

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. An acoustophoretic device for clarifying a discrete volume of fluid, comprising:
   a substantially acoustically transparent container; and
   a separation unit configured to receive the container and including (i) at least one ultrasonic transducer having a piezoelectric material driven by a voltage signal to create a multi-dimensional acoustic standing wave.

2. The device of claim 1, wherein the container comprises plastic, glass, polycarbonate, low-density polyethylene, or high-density polyethylene.

3. The device of claim 1, wherein the at least one ultrasonic transducer is at least a first ultrasonic transducer and a second ultrasonic transducer, wherein the first ultrasonic transducer is driven to form a planar acoustic standing wave, and wherein the second ultrasonic transducer is driven to form the multi-dimensional acoustic standing wave.

4. The device of claim 1, wherein the multi-dimensional acoustic standing wave results in an acoustic radiation force that includes an axial force component and a lateral force component that are of the same order of magnitude.

5. The device of claim 1, further comprising a support structure for moving the container and the at least one ultrasonic transducer relative to each other.

6. The device of claim 5, further comprising a wall in the separation unit, wherein the support structure moves the at least one ultrasonic transducer vertically along one wall of the separation unit.

7. The device of claim 5, further comprising a wall in the separation unit, wherein the at least one ultrasonic transducer is fixed in position on the at least one wall of the separation unit, and the separation unit moves relative to the container.

8. The device of claim 1, further comprising a wall in the separation unit, wherein the separation unit is sized so as to provide an interstitial space between the at least one wall and the container.

9. The device of claim 1, wherein the at least one ultrasonic transducer is a plurality of ultrasonic transducers located on a common wall of the separation unit or located opposite each other.

10. The device of claim 1, further comprising a reflector located on a wall of the separation unit opposite the at least one ultrasonic transducer.

11. A method for separating a second fluid or particulate from a host fluid, comprising:
    placing a substantially acoustically transparent container containing a discrete volume of the mixture of the host fluid and the second fluid or particulate into a a separation unit, wherein the separation unit includes at least one ultrasonic transducer configured to create an acoustic standing wave; and
    driving the at least one ultrasonic transducer to create the acoustic standing wave in the container, such that the second fluid or particulate is trapped in the acoustic standing wave, clumps, clusters, agglomerates, or coalesces together, and continuously rises or settles out of the host fluid due to buoyancy or gravity forces.

12. The method of claim 11, wherein the particulate is Chinese hamster ovary (CHO) cells, NS0 hybridoma cells, baby hamster kidney (BHK) cells, insect cells, or human cells.

13. The method of claim 11, further comprising placing a fluid in an interstitial space between the at least one transducer and the container prior to driving the at least one ultrasonic transducer.

14. The method of claim 11, further comprising moving the container and the separation unit relative to each other to sweep the non-flowing mixture from a lower end of the container to an upper end of the container or to sweep the non-flowing mixture from the upper end of the container to the lower end of the container.

15. The method of claim 14, wherein the container and the separation unit move relative to each other at a linear velocity of from about 0.1 millimeter/second to about 1 centimeter/second.

16. The method of claim 14, wherein the at least one ultrasonic transducer comprises:
    a housing having a top end, a bottom end, and an interior volume; and
    a piezoelectric element at the bottom end of the housing that includes an exposed exterior surface and an interior surface, the piezoelectric element being able to vibrate when driven by a voltage signal.

17. The method of claim 16, wherein a backing layer contacts the interior surface of the piezoelectric element, the backing layer being made of a substantially acoustically transparent material.

18. The method of claim 16, wherein the at least one ultrasonic transducer is at least a first ultrasonic transducer and a second ultrasonic transducer located on a common wall of the separation unit;
    wherein the first ultrasonic transducer is driven to form a planar acoustic standing wave; and
    wherein the second ultrasonic transducer is driven to form a multi-dimensional acoustic standing wave.

19. An acoustophoretic device for clarifying a non-flowing fluid, comprising:
- a disposable separation bag including an exterior surface and an interior volume bounded by the exterior surface; and
- an ultrasonic transducer at least partially disposed inward of the exterior surface of the separation bag, the ultrasonic transducer including a piezoelectric material configured to be driven by a voltage signal to create an acoustic standing wave within the interior volume of the disposable separation bag.

20. The device of claim 19, wherein the separation bag is made from at least two layers of differentially functioning polymers, the ultrasonic transducer being disposed between the at least two layers.

* * * * *